(12) United States Patent
Chen et al.

(10) Patent No.: US 12,586,186 B2
(45) Date of Patent: Mar. 24, 2026

(54) JAUNDICE ANALYSIS SYSTEM AND METHOD THEREOF

(71) Applicants: Chieh-Hsiao Chen, Taichung City (TW); Yu-Hsuan Chen, Taichung City (TW)

(72) Inventors: Chieh-Hsiao Chen, Taichung City (TW); Yu-Hsuan Chen, Taichung City (TW)

(73) Assignees: Chieh-Hsiao Chen, Taichung City (TW); Yu-Hsuan Chen, Taichung City (TW)

( * ) Notice: Subject to any disclaimer, the term of this patent is extended or adjusted under 35 U.S.C. 154(b) by 434 days.

(21) Appl. No.: 18/267,909

(22) PCT Filed: Dec. 18, 2020

(86) PCT No.: PCT/CN2020/137680
§ 371 (c)(1),
(2) Date: Jun. 16, 2023

(87) PCT Pub. No.: WO2022/126622
PCT Pub. Date: Jun. 23, 2022

(65) Prior Publication Data
US 2024/0054641 A1 Feb. 15, 2024

(51) Int. Cl.
*G06T 7/00* (2017.01)
*A61B 5/103* (2006.01)
(Continued)

(52) U.S. Cl.
CPC .......... *G06T 7/0012* (2013.01); *A61B 5/1032* (2013.01); *G06T 3/60* (2013.01);
(Continued)

(58) Field of Classification Search
CPC .................... G06T 7/0012; G06T 3/60; G06T 2207/20081; G06T 2207/20084;
(Continued)

(56) References Cited

U.S. PATENT DOCUMENTS 7,187,790 B2 3/2007 Sabol et al.
2015/0359459 A1* 12/2015 Taylor .................. A61B 5/0077
600/477
(Continued)

FOREIGN PATENT DOCUMENTS

CN 104856680 A 8/2015
CN 105466864 A 4/2016
(Continued)

OTHER PUBLICATIONS

International Search Report from International Application No. PCT/CN2020/137680.
(Continued)

*Primary Examiner* — Van D Huynh
(74) *Attorney, Agent, or Firm* — Haverstock & Owens, A Law Corporation

(57) ABSTRACT

A jaundice analysis system includes a database and a processing device for accessing the database. The processing device includes: a data processing module for generating a training data according to an image data, correlating the training data with a category data, and storing the training data in the database; and a deep learning module for training a target convolutional neural network module with the training data correlating with the category data to obtain a trained convolutional neural network module. The image data includes a first sclera image. The trained convolutional neural network module of the processing device generates a testing data according to an input image data. The input image data includes a second sclera image of a target subject. The testing data indicates the target subject's bilirubin concentration range.

18 Claims, 7 Drawing Sheets

(51) Int. Cl.
    *G06T 3/60*           (2006.01)
    *G16H 30/40*        (2018.01)

(52) U.S. Cl.
    CPC ... *G16H 30/40* (2018.01); *G06T 2207/20081*
        (2013.01); *G06T 2207/20084* (2013.01); *G06T*
        *2207/30041* (2013.01)

(58) Field of Classification Search
    CPC ........ G06T 2207/30041; A61B 5/1032; A61B
            2576/02; A61B 5/1455; A61B 5/4244;
            A61B 5/7267; G16H 30/40; G06V 10/82;
                                 G06V 40/18
    See application file for complete search history.

(56) References Cited

U.S. PATENT DOCUMENTS

| | | | | |
|---|---|---|---|---|
| 2018/0177434 | A1* | 6/2018 | Kim | ...................... A61B 5/6898 |
| 2019/0110716 | A1* | 4/2019 | Sunwoo | ................... A61B 3/10 |
| 2019/0343426 | A1* | 11/2019 | Vartdal | ................ A61B 5/1032 |
| 2020/0121228 | A1* | 4/2020 | Taylor | ...................... A61B 5/00 |
| 2020/0229969 | A1* | 7/2020 | Fix | ........................... G06V 20/20 |
| 2022/0020118 | A1* | 1/2022 | Hallen | ..................... A61B 3/13 |
| 2023/0162359 | A1* | 5/2023 | Choi | ........................ A61B 3/00 |
| | | | | 382/128 |
| 2023/0255475 | A1* | 8/2023 | Van Saarloos | ..... G01B 11/2513 |
| | | | | 351/212 |

FOREIGN PATENT DOCUMENTS

| | | |
|---|---|---|
| CN | 108430326 A | 8/2018 |
| CN | 109009132 A | 12/2018 |
| WO | 2022126622 A | 6/2022 |

OTHER PUBLICATIONS

Written Opinion from International Application No. PCT/CN2020/137680.

* cited by examiner

302

304

402

502

504

602

604

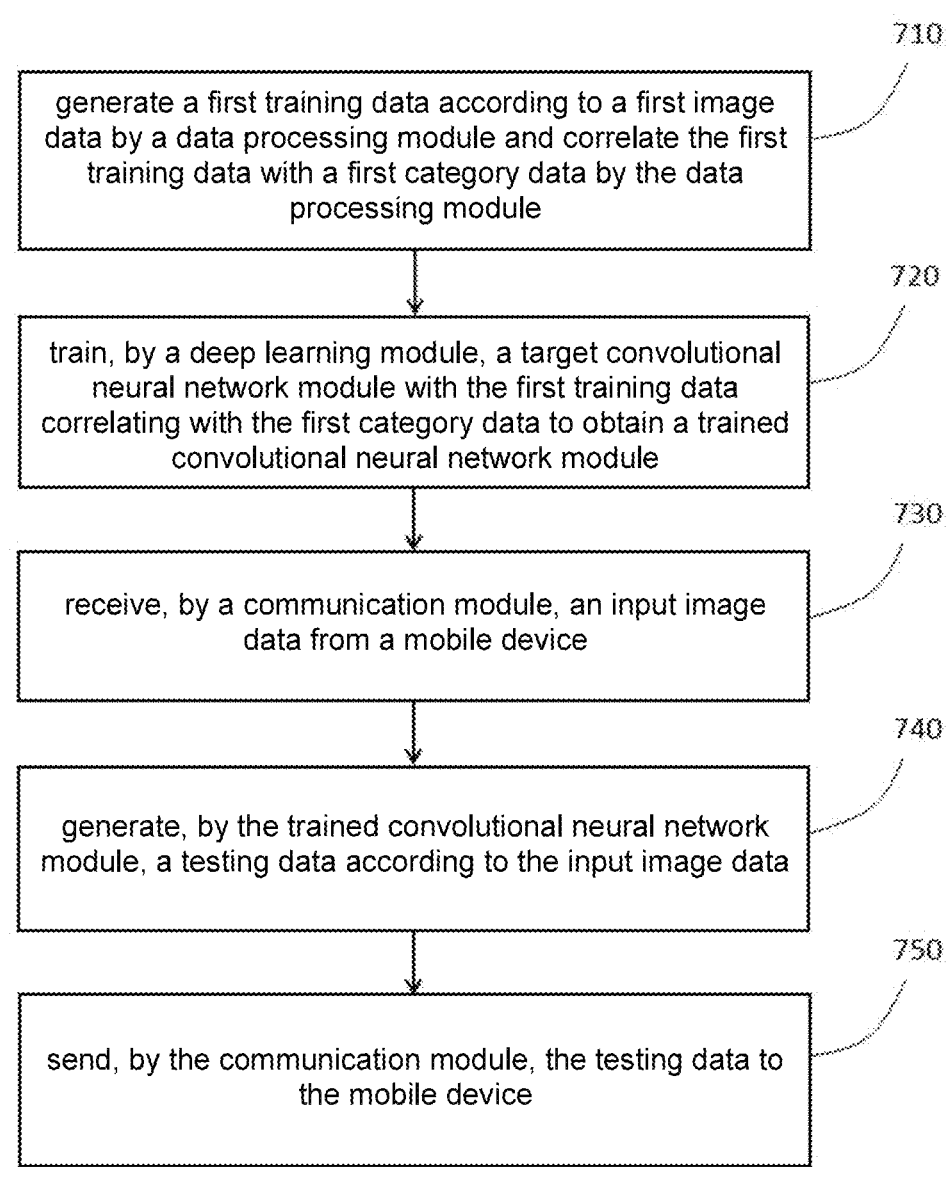

700

710 generate a first training data according to a first image data by a data processing module and correlate the first training data with a first category data by the data processing module

720 train, by a deep learning module, a target convolutional neural network module with the first training data correlating with the first category data to obtain a trained convolutional neural network module

730 receive, by a communication module, an input image data from a mobile device

740 generate, by the trained convolutional neural network module, a testing data according to the input image data

750 send, by the communication module, the testing data to the mobile device

FIG.7

JAUNDICE ANALYSIS SYSTEM AND METHOD THEREOF

BACKGROUND OF THE INVENTION

Field of the Invention

The present disclosure relates to jaundice analysis systems and methods, and more particularly to a jaundice analysis system and method for determining whether a target subject has jaundice symptoms according to the target subject's sclera images.

Description of the Prior Art

Compared with other metabolic diseases, jaundice comes with unique symptoms like a yellow tinge to the skin and sclera. However, it is likely for patients with jaundice symptoms to ignore their diseases or organ failure when they were born to have a yellowish complexion or they mistake their jaundice complexion for a tanned complexion. As a result, early diagnosis of their jaundice or organ degeneration is unlikely. Therefore, it is imperative to provide a jaundice analysis system and method for determining whether a target subject has jaundice symptoms according to the target subject's sclera images.

SUMMARY OF THE INVENTION

In view of the aforesaid drawback of the prior art, it is an objective of the disclosure to provide a jaundice analysis system and method for determining whether a target subject has jaundice symptoms according to the target subject's sclera images.

To achieve the above and other objectives, the disclosure provides a jaundice analysis system comprising a database and a processing device for accessing the database. The processing device comprises: a data processing module for generating a first training data according to a first image data, correlating the first training data with a first category data, and storing the first training data in the database; and a deep learning module for training a target convolutional neural network module with the first training data correlating with the first category data to obtain a trained convolutional neural network module. The first image data comprises a first sclera image. The database is communicatively connected to the data processing module and/or the deep learning module. The trained convolutional neural network module of the processing device generates a testing data according to an input image data. The input image data comprises a second sclera image of a target subject. The testing data indicates a bilirubin concentration range of the target subject.

In a preferred embodiment of the disclosure, the deep learning module obtains the trained convolutional neural network module by transfer learning. Thus, the target convolutional neural network module is a trained convolutional neural net work module (with the training being not restricted to detecting jaundice symptoms or determining bilirubin concentration).

In a preferred embodiment of the disclosure, the data processing module performs first cutting processing on the first image data to generate a first cutting image data and generates the first training data according to the first cutting image data.

In a preferred embodiment of the disclosure, the data processing module performs mirroring processing on the first image data to generate a mirroring image data and generates the first training data according to the mirroring image data.

In a preferred embodiment of the disclosure, the data processing module performs second cutting processing on the mirroring image data to generate a second cutting image data and generates the first training data according to the second cutting image data, with the second cutting image data having a specific image shape.

In a preferred embodiment of the disclosure, the data processing module performs third cutting processing on the second cutting image data to generate a third cutting image data and generates the first training data according to the third cutting image data.

In a preferred embodiment of the disclosure, the data processing module performs de-reflection processing on the first image data to generate a de-reflection image data and generates the first training data according to the de-reflection image data.

In a preferred embodiment of the disclosure, the data processing module generates a second image data according to the first image data, generates a second training data according to the second image data, correlates the second training data with a second category data, and stores the second training data in the database, wherein the deep learning module trains the target convolutional neural network module with the first training data correlating with the first category data and the second training data correlating with the second category data to obtain the trained convolutional neural network module.

In a preferred embodiment of the disclosure, the data processing module performs one of image translating processing, image rotating processing and image flipping processing on the first image data to generate the second image data.

In a preferred embodiment of the disclosure, the jaundice analysis system further comprises a mobile device for storing the input image data, and the processing device further comprises a communication module communicatively connected to the mobile device and the trained convolutional neural network module of the processing device. The communication module receives the input image data from the mobile device and sends the testing data to the mobile device.

To achieve the above and other objectives, the disclosure further provides a jaundice analysis method applicable to a jaundice analysis system, the jaundice analysis method comprising the steps of: generating a first training data according to a first image data by a data processing module of the jaundice analysis system and correlating the first training data with a first category data by the data processing module; training a target convolutional neural network module with the first training data correlating with the first category data by a deep learning module of the jaundice analysis system to obtain a trained convolutional neural network module; and generating a testing data according to an input image data by the trained convolutional neural network module of the jaundice analysis system. The input image data comprises a second sclera image of a target subject. The first image data comprises a first sclera image. The testing data indicates a bilirubin concentration range of the target subject.

In a preferred embodiment of the disclosure, the deep learning module obtains the trained convolutional neural network module by transfer learning. Thus, the target convolutional neural network module is a trained convolutional neural network module (with the training being not restricted to detecting jaundice symptoms or determining bilirubin concentration but being adapted to include, for example, detecting other matters according to related images, but the disclosure being not limited thereto).

In a preferred embodiment of the disclosure, the generating the first training data according to the first image data further comprises performing first cutting processing on the first image data by the data processing module to generate a first cutting image data, and the data processing module generates the first training data according to the first cutting image data.

In a preferred embodiment of the disclosure, the generating the first training data according to the first image data further comprises performing mirroring processing on the first image data by the data processing module to generate a mirroring image data, and the data processing module generates the first training data according to the mirroring image data.

In a preferred embodiment of the disclosure, the generating the first training data according to the first image data further comprises performing second cutting processing on the mirroring image data by the data processing module to generate a second cutting image data, and the data processing module generates the first training data according to the second cutting image data, with the second cutting image data having a specific image shape.

In a preferred embodiment of the disclosure, the generating the first training data according to the first image data further comprises performing third cutting processing on the second cutting image data by the data processing module to generate a third cutting image data, and the data processing module generates the first training data according to the third cutting image data.

In a preferred embodiment of the disclosure, the generating the first training data according to the first image data further comprises performing de-reflection processing on the first image data by the data processing module to generate a de-reflection image data, and the data processing module generates the first training data according to the de-reflection image data.

In a preferred embodiment of the disclosure, the jaundice analysis method further comprises the steps of: generating, by the data processing module, a second image data according to the first image data; and generating a second training data according to the second image data by the data processing module and correlating the second training data with a second category data by the data processing module, wherein the deep learning module trains the target convolutional neural network module with the first training data correlating with the first category data and the second training data correlating with the second category data to obtain the trained convolutional neural network module.

In a preferred embodiment of the disclosure, the data processing module performs one of image translating processing, image rotating processing and image flipping processing on the first image data to generate the second image data.

In a preferred embodiment of the disclosure, the jaundice analysis method further comprises the steps of: receiving, by a communication module of the jaundice analysis system, the input image data from a mobile device; and sending, by the communication module, the testing data to the mobile device.

The aforesaid aspects and other aspects of the disclosure are illustrated by non-restrictive specific embodiments, depicted by accompanying drawings and described below.

BRIEF DESCRIPTION OF THE DRAWINGS

FIG. 7 is a schematic view of a process flow of a jaundice analysis method in a specific embodiment of the disclosure.

DETAILED DESCRIPTION OF THE EMBODIMENTS

Figure 1:
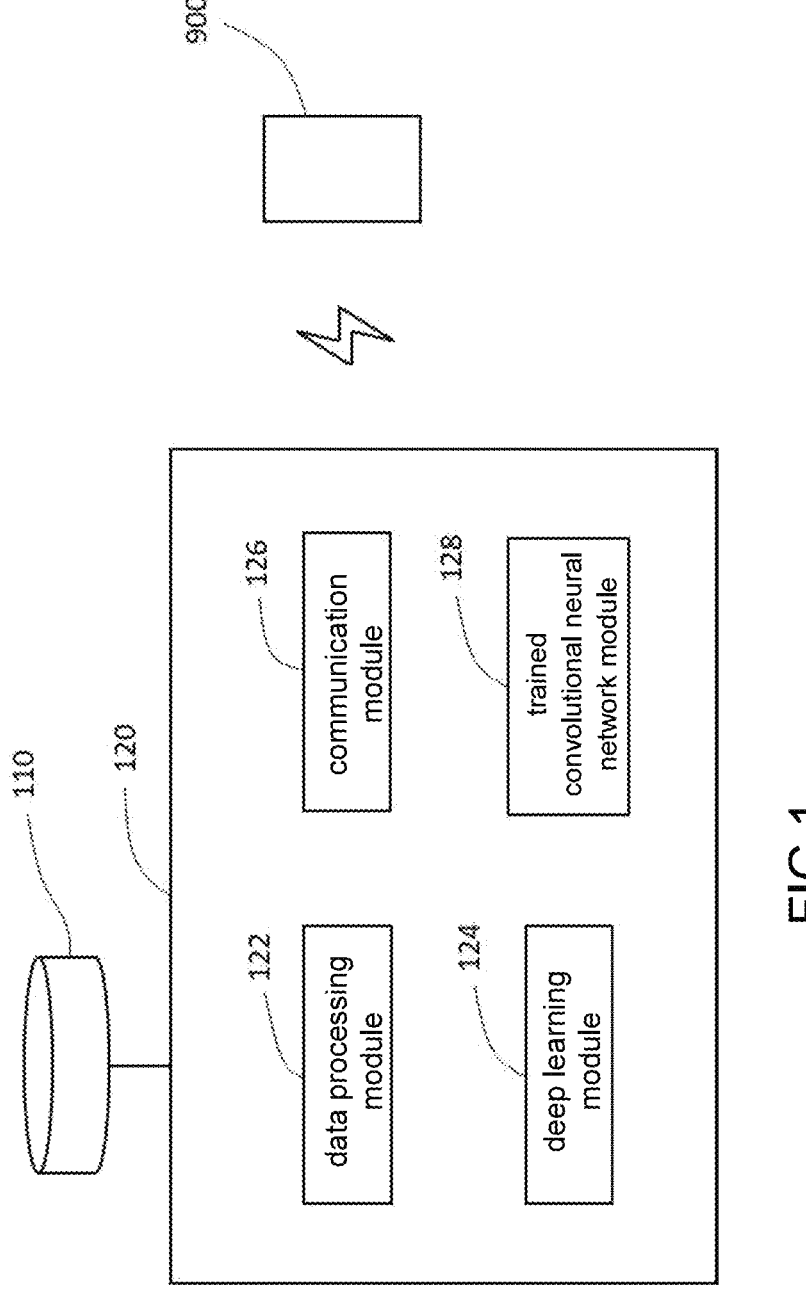
FIG. 1 is a block diagram of a jaundice analysis system in a specific embodiment of the disclosure.

Referring to FIG. 1, there is shown a block diagram of a jaundice analysis system 100 in a specific embodiment of the disclosure. In the embodiment illustrated by FIG. 1, the jaundice analysis system 100 comprises a database 110 and a processing device 120. The processing device 120 can access the database 110 and thus is communicatively connected to the database 110. The processing device 120 comprises a data processing module 122 and a deep learning module 124. Preferably, the data processing module 122 is communicatively connected to the database 110, and the deep learning module 124 is communicatively connected to the database 110. In the embodiment illustrated by FIG. 1, the data processing module 122 generates a first training data according to a first image data, associates the first training data with a first category data, and stores the first training data in the database 110. The first image data comprises a first sclera image. The first category data indicates a bilirubin concentration level or a bilirubin concentration range. Note that jaundice stems from excess amounts of bilirubin circulating in the blood and leads to a yellowish appearance of the skin, sclera, and mucous membranes. Therefore, the bilirubin concentration level or the bilirubin concentration range reflects the extent of jaundice symptoms; in other words, the first category data indicates the extent of jaundice symptoms. In a specific embodiment, the first image data is stored in the database 110.

Note that the data processing module 122 generates different first training data according to different first image data, with the different first training data correlating with the different first category data, respectively. Optionally, the different first training data each correlate with the same first category data. For instance, the data processing module 122 generate a first group of first training data according to a first group of first image data, and each first training data in the first group of first training data correlates with a first category data indicative of a first bilirubin concentration range. The data processing module 122 generates a second group of first training data according to a second group of first image data, and each first training data in the second group of first training data correlates with another first category data indicative of a second bilirubin concentration range. The first bilirubin concentration range is different from the second bilirubin concentration range. In a specific embodiment, the first image data has already correlated with the first category data before the processing device 120 or the data processing module 122 receives the first image data (for example, from the database 110), and the data processing module 122 correlates the first training data generated according to the first image data with the first category data.

In the embodiment illustrated by FIG. 1, the deep learning module 124 uses the first training data correlating with the first category data to train a target convolutional neural network module and thereby obtain (or generate) a trained convolutional neural network module 128. Preferably, the deep learning module 124 obtains the trained convolutional neural network module 128 by transfer learning. Thus, the target convolutional neural network module becomes a trained convolutional neural network module. In a specific embodiment, the deep learning module 124 undergoes transfer learning according to EfficientNetB5. Note that the trained convolutional neural network module 128 generated by the deep learning module 124 is also included in the processing device 120. Thus, the trained convolutional neural network module 128 of the processing device 120 generates a testing data according to an input image data. The input image data comprises a second sclera image of a target subject. The testing data indicates a bilirubin concentration range of the target subject.

In a specific embodiment, the deep learning module 124 generates various filters on its own to capture different eigenvalues in the course of training a target convolutional neural network module with the first training data correlating with the first category data. The filters are, for example, Histogram filters, Clahe (Adaptive Histogram) filters and Guassian filters, but the disclosure is not limited thereto. In a specific embodiment, the deep learning module 124 is communicatively connected to the target convolutional neural network module and the trained convolutional neural network module 128. In a specific embodiment, the deep learning module 124 comprises the target convolutional neural network module and the trained convolutional neural network module 128. In a specific embodiment, the data processing module 122 is communicatively connected to the deep learning module 124 and/or the trained convolutional neural network module 128.

In a specific embodiment, the data processing module 122 generates a second image data according to the first image data and generates a second training data according to the second image data to obtain more training data and thereby enhance the precision of analysis performed by the trained convolutional neural network module 128 on the bilirubin concentration range or jaundice extent. Then, the data processing module 122 correlates the second training data with a second category data and stores the second training data in the database 110. Preferably, the second category data is the first category data correlating with the first image data. In a specific embodiment, the deep learning module 124 trains the target convolutional neural network module with the first training data correlating with the first category data and the second training data correlating with the second category data to obtain the trained convolutional neural network module 128.

In a variant specific embodiment, the data processing module 122 performs image translating processing on the first image data (for example, various translating processing, such as horizontal translating and vertical translating, on the first image data, but the disclosure is not limited thereto), image rotating processing on the first image data (for example, 0~180 degrees of rotating processing on the first image data, but the disclosure is not limited thereto), image flipping processing on the first image data (for example, various flipping processing, such as horizontal flipping and vertical flipping, on the first image data, but the disclosure is not limited thereto), or gap compensation constant processing on the first image data to generate the second image data. Note that the disclosure is not restrictive of the way of generating the second image data by the data processing module 122 according to the first image data.

In a specific embodiment, the processing device 120 further comprises a communication module 126. The processing module 122 receives a data (for example, an input image data) from a device 900 through the communication module 126 or sends a data (for example, a testing data) to the device 900 through the communication module 126. The communication module 126 is communicatively connected to the device 900 and the trained convolutional neural network module 128 of the processing device 120. The device 900 is, for example, a computer, a mobile device (alternatively provided in the form of a computer) or a remote server, but the disclosure is not limited thereto. In a specific embodiment, the device 900 is regarded as a portion of the jaundice analysis system 100, and the input image data is stored in the device 900. In a specific embodiment, the device 900 comprises an image capturing device whereby the device 900 captures images and generates the input image data. Preferably, the input image data comprises a first input image data and a second input image data. The first input image data comprises a left sclera image of the target subject. The second input image data comprises a right sclera image of the target subject. In a specific embodiment, the communication module 126 is communicatively connected to the data processing module 122 and/or the deep learning module 124.

In a specific embodiment, the jaundice analysis system 100 of the disclosure comprises one or more processors and implements the database 110 and the processing device 120 through hardware-software synergy. In a specific embodiment, the processing device 120 comprises one or more processors and implements the data processing module 122, the deep learning module 124, the communication module 126 and the trained convolutional neural network module 128 through hardware-software synergy. In a specific embodiment, the device 900 comprises one or more processors and implements the image capturing device through hardware-software synergy.

Figures 2A, 2B, 2C:
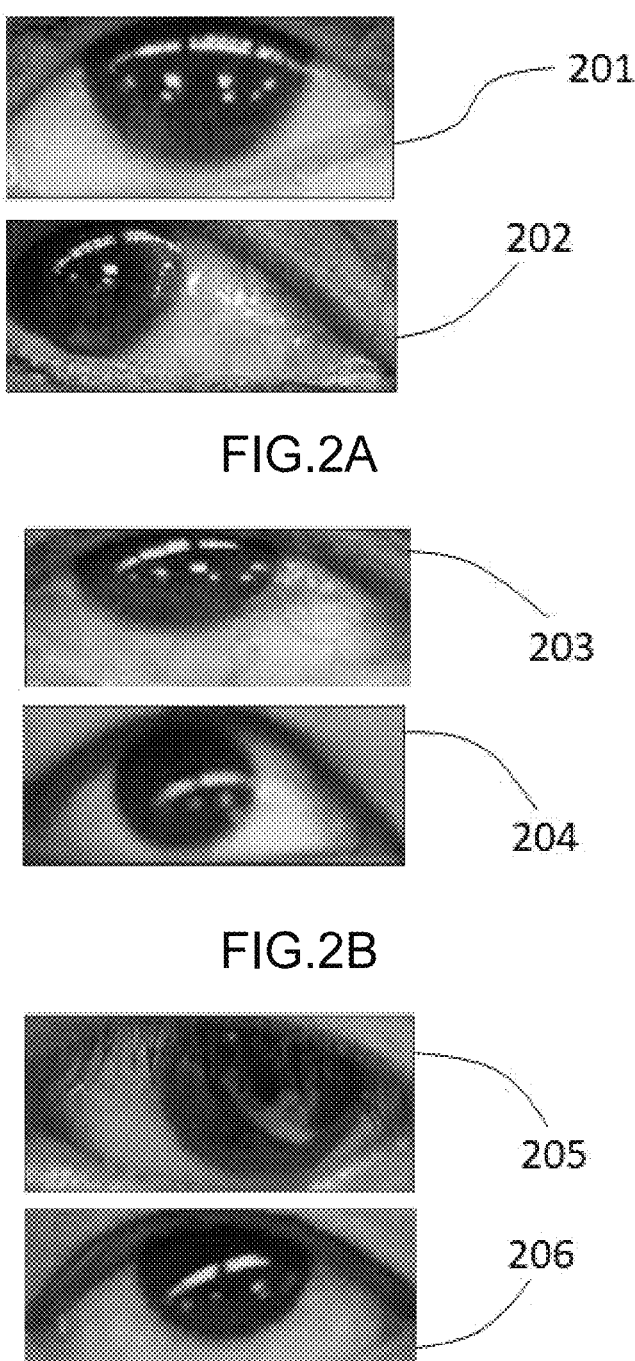
FIG. 2A is a schematic view of a first image data in a specific embodiment.
FIG. 2B is a schematic view of the first image data in a specific embodiment.
FIG. 2C is a schematic view of the first image data in a specific embodiment.

Referring to FIG. 2A through FIG. 2C, there are shown different first image data. The first category data correlating with first image data 201, 202 of FIG. 2A indicates a bilirubin concentration range of 0~1.2 mg/dL. The first category data correlating with first image data 203, 204 of FIG. 2B indicates a bilirubin concentration range of 1.3~3.5 mg/dL. The first category data correlating with first image data 205, 206 of FIG. 2C indicates a bilirubin concentration range greater than 3.6 mg/dL. In a specific embodiment, the data processing module of the jaundice analysis system 100 of the disclosure performs first cutting processing on the first image data to generate a first cutting image data and thereby cut or adjust the first image data so as for the first image data to assume identical image size. The data processing module generates the first training data according to the first cutting image data.

Figure 3:
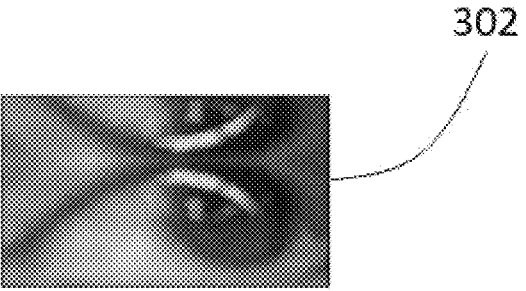
FIG. 3 is a schematic view of a mirroring image data in a specific embodiment.
Figure 3:
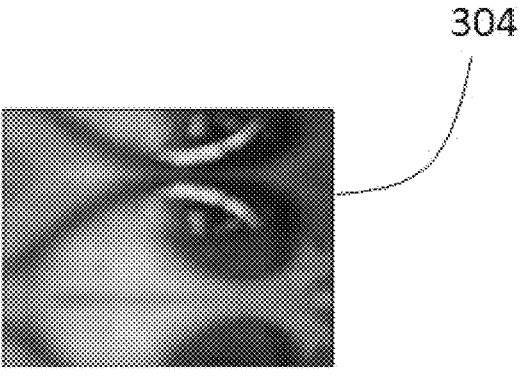

Referring to FIG. 3, there are shown different mirroring image data 302, 304. The mirroring image data 302, 304 are generated when the data processing module performs different mirroring processing on the first image data. The short side of the image data 304 is supplemented by performing mirroring processing (with the short side functioning as the axis of symmetry) to render the length and width of the image data 304 equal. In a specific embodiment, the first cutting image data is regarded as a first image data. Thus, the data processing module performs mirroring processing on the first image data which has undergone first cutting processing. In a specific embodiment, the data processing module generates the first training data according to the mirroring image data.

Figure 4:
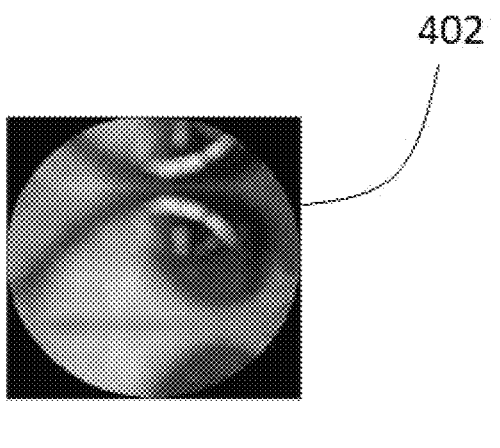
FIG. 4 is a schematic view of a second cutting image data in a specific embodiment.

Referring to FIG. 4, there is shown a schematic view of a second cutting image data in a specific embodiment. In the embodiment illustrated by FIG. 4, the data processing module performs second cutting processing on the mirroring image data 304 of FIG. 3 to generate a second cutting image data 402. In a specific embodiment, the cutting of the second cutting processing involves using one side of the mirroring image data 304 as the diameter of a tangent circle (a circle inscribed in a square), cutting out the image content outside the tangent circle and keeping the image content inside the tangent circle. Thus, the data processing module cuts different mirroring image data so as for the different mirroring image data to assume identical image size. Note that FIG. 4 merely serves exemplary purposes; thus, the purpose of performing the second cutting processing by the data processing module is not restricted to cutting an image so as for the image to assume a round shape. In a variant embodiment, an image is cut such that the image assumes a specific image shape as needed. In a specific embodiment, the data processing module generates the first training data according to the second cutting image data.

Figure 5:
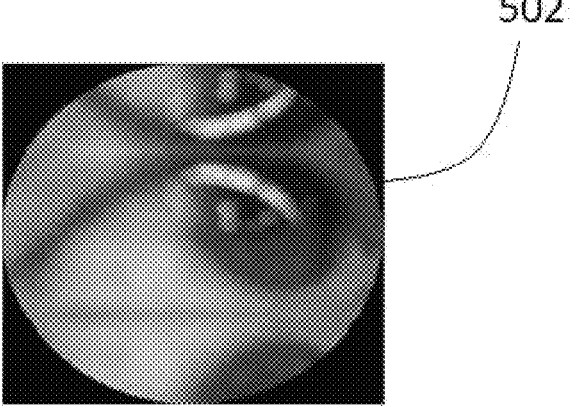
FIG. 5 is a schematic view of how to generate a third cutting image data in a specific embodiment.
Figure 5:
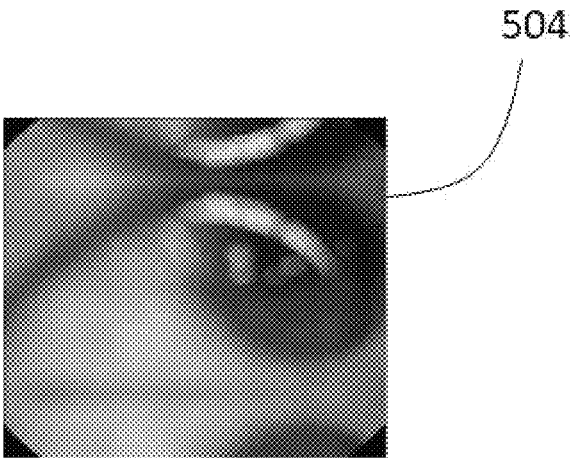

Referring to FIG. 5, there is shown a schematic view of how to generate a third cutting image data in a specific embodiment. In the embodiment illustrated by FIG. 5, the data processing module performs third cutting processing on a second cutting image data 502 to generate a third cutting image data 504. In a specific embodiment, the cutting of the third cutting processing involves using the center of the second cutting image data 502 to take a square of a specific size and keeping the image content inside the square with a view to reducing unnecessary features. In a specific embodiment, the data processing module generates the first training data according to the third cutting image data.

Figure 6:
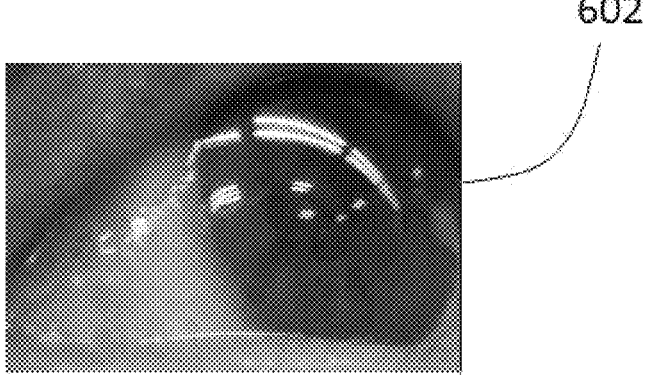
FIG. 6 is a schematic view of how to generate a de-reflection image data in a specific embodiment.
Figure 6:
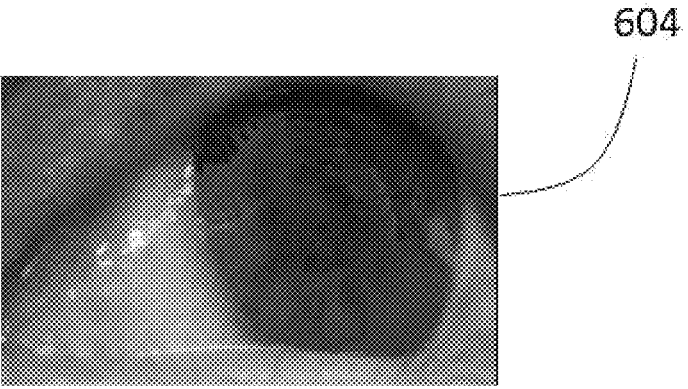

Referring to FIG. 6, there is shown a schematic view of how to generate a de-reflection image data in a specific embodiment. In the embodiment illustrated by FIG. 6, the data processing module performs de-reflection processing on a first image data 602 to generate a de-reflection image data 604. Thus, this embodiment, it is feasible to prevent the white portion of the eyeball reflection light in the image from interfering with the deep learning and thereby enable the deep learning module to train the target convolutional neural network module. In a specific embodiment, the de-reflection processing is performed by removing the eyeball reflection light portion with the imitation function of PhotoImpact. In a specific embodiment, the data processing module generates the first training data according to the de-reflection image data.

Note that the first cutting image data, the mirroring image data, the second cutting image data, the third cutting image data and the de-reflection image data are regarded as the first image data and the data processing module and are able to perform the first cutting processing, mirroring processing, second cutting processing, third cutting processing and/or de-reflection processing on the image data.

Referring to FIG. 7, there is shown a schematic view of a process flow of a jaundice analysis method 700 in a specific embodiment of the disclosure. In the embodiment illustrated by FIG. 7, the jaundice analysis method 700 is applicable to the jaundice analysis system 100. The jaundice analysis method 700 starts with step 710 in which the data processing module of the jaundice analysis system 100 generates a first training data according to a first image data and correlates the first training data with a first category data. The first image data comprises a first sclera image. Then, in step 720, the deep learning module of the jaundice analysis system 100 trains a target convolutional neural network module with the first training data correlating with the first category data to obtain a trained convolutional neural network module. In a specific embodiment, the deep learning module obtains the trained convolutional neural network module by transfer learning. Thus, the target convolutional neural network module is a trained convolutional neural network module, with the target convolutional neural network module being previously trained and being not restricted to detecting jaundice symptoms or determining bilirubin concentration but being adapted to include, for example, detecting other matters according to related images, but the disclosure being not limited thereto.

In step 730, the communication module of the jaundice analysis system 100 receives an input image data from a mobile device (for example, a cellphone or tablet, but the disclosure is not limited thereto). The input image data comprises a second sclera image of a target subject. Preferably, the input image data comprises a first input image data and a second input image data. The first input image data comprises a left sclera image of the target subject. The second input image data comprises a right sclera image of the target subject. Note that step 730 may precede step 710 or step 720 as needed.

Step 710 through step 730 are followed by step 740. In step 740, the trained convolutional neural network module of the jaundice analysis system 100 generates a testing data according to the input image data. The testing data indicates a bilirubin concentration range of the target subject. The bilirubin concentration range reflects the extent of jaundice. Then, in step 750, the communication module of the jaundice analysis system 100 sends the testing data to the mobile device.

In a specific embodiment, the generating the first training data according to the first image data further comprises performing first cutting processing on the first image data by the data processing module to generate the first cutting image data. The data processing module generates the first training data according to the first cutting image data. In a specific embodiment, the data processing module performs the first cutting processing on the first image data according to a first command. The first command is, for example, an image cutting operation performed by a user with a mouse or is, for example, a default image cutting command, but the disclosure is not limited thereto.

In a specific embodiment, the generating the first training data according to the first image data further comprises performing mirroring processing on the first image data by the data processing module to generate a mirroring image data. The data processing module generates the first training data according to the mirroring image data. In a specific embodiment, the data processing module performs the mirroring processing on the first image data according to a second command. The second command is, for example, an image mirroring operation performed by a user with a mouse or is, for example, a default image mirroring command, but the disclosure is not limited thereto.

In a specific embodiment, the generating the first training data according to the first image data further comprises performing second cutting processing on the mirroring image data by the data processing module to generate the second cutting image data. The second cutting image data has a specific image shape. The data processing module generates the first training data according to the second cutting image data. In a specific embodiment, the data processing module performs the second cutting processing on the mirroring image data according to a third command. The third command is, for example, an image cutting operation performed by a user with a mouse or, for example, a default image cutting command, but the disclosure is not limited thereto.

In a specific embodiment, the generating the first training data according to the first image data further comprises performing the third cutting processing on the second cutting image data by the data processing module to generate the third cutting image data. The data processing module generates the first training data according to the third cutting image data. In a specific embodiment, the data processing module performs the third cutting processing on the second cutting image data according to a fourth command. The fourth command is, for example, an image cutting operation performed by a user with a mouse or is, for example, a default image cutting command, but the disclosure is not limited thereto.

In a specific embodiment, the generating the first training data according to the first image data further comprises performing the de-reflection processing on the first image data by the data processing module to generate a de-reflection image data. The data processing module generates the first training data according to the de-reflection image data. In a specific embodiment, the data processing module performs the de-reflection processing on the first image data according to a fifth command. The fifth command is, for example, an image de-reflection operation performed by a user with a mouse or is, for example, a default image de-reflection command, but the disclosure is not limited thereto.

In a specific embodiment, to obtain more training data and thereby enhance the precision of analysis performed by the trained convolutional neural network module on the bilirubin concentration range or jaundice extent, the jaundice analysis method 700 further comprises: generating, by the data processing module, the second image data according to the first image data; and generating a second training data according to the second image data by the data processing module and correlating the second training data with a second category data by the data processing module. Preferably, the second category data is the first category data correlating with the first image data. In a specific embodiment, the deep learning module trains the target convolutional neural network module with the first training data correlating with the first category data and the second training data correlating with the second category data to obtain the trained convolutional neural network module.

In a variant specific embodiment, the data processing module performs a processing means of one of the image translating processing, image rotating processing, image flipping processing and gap compensation constant processing on the first image data to generate the second image data. Note that the disclosure is not restrictive of the way of generating the second image data by the data processing module according to the first image data.

Therefore, a jaundice analysis system and method of the disclosure are illustrated by the accompanying drawings and explained above. Specific embodiments of the disclosure merely serve illustrative purposes; thus, various changes can be made to the specific embodiments of the disclosure without departing from the spirit and scope of the claims of the disclosure and shall fall within the scope of the claims of the disclosure. Therefore, the specific embodiments of the disclosure are not restrictive of the disclosure, allowing the spirit and scope of the disclosure to be defined by the appended claims.

What is claimed is:

1. A jaundice analysis system, comprising:
   a database; and
   a processing device for accessing the database, the processing device comprising:
      a data processing module for generating a first training data according to a first image data, correlating the first training data with a first category data, and storing the first training data in the database; and
      a deep learning module for training a target convolutional neural network module with the first training data correlating with the first category data to obtain a trained convolutional neural network module,
   wherein the first image data comprises a first sclera image,
   wherein the database communicatively connects to the data processing module and/or the deep learning module,
   wherein the trained convolutional neural network module of the processing device generates a testing data according to an input image data, with the input image data including a second sclera image of a target subject,
   wherein the testing data indicates a bilirubin concentration range of the target subject;
   wherein the data processing module performs mirroring processing on the first image data to generate a mirroring image data and generates the first training data according to the mirroring image data.

2. The jaundice analysis system of claim 1, wherein the deep learning module obtains the trained convolutional neural network module by transfer learning.

3. The jaundice analysis system of claim 1, wherein the data processing module performs first cutting processing on the first image data to generate a first cutting image data and generates the first training data according to the first cutting image data.

4. The jaundice analysis system of claim 1, wherein the data processing module performs second cutting processing on the mirroring image data to generate a second cutting image data and generates the first training data according to the second cutting image data, with the second cutting image data having a specific image shape.

5. The jaundice analysis system of claim 4, wherein the data processing module performs third cutting processing on the second cutting image data to generate a third cutting image data and generates the first training data according to the third cutting image data.

6. The jaundice analysis system of claim 1, wherein the data processing module performs de-reflection processing on the first image data to generate a de-reflection image data and generates the first training data according to the de-reflection image data.

7. The jaundice analysis system of claim 1, wherein the data processing module generates a second image data according to the first image data, generates a second training data according to the second image data, correlates the second training data with a second category data, and stores the second training data in the database, wherein the deep learning module trains the target convolutional neural network module with the first training data correlating with the first category data and the second training data correlating with the second category data to obtain the trained convolutional neural network module.

8. The jaundice analysis system of claim 7, wherein the data processing module performs one of image translating processing, image rotating processing and image flipping processing on the first image data to generate the second image data.

9. The jaundice analysis system of claim 1, further comprising:

a mobile device for storing the input image data, wherein the processing device further comprises:

a communication module communicatively connected to the mobile device and the trained convolutional neural network module of the processing device and adapted to receive the input image data from the mobile device and send the testing data to the mobile device.

10. A jaundice analysis method applicable to a jaundice analysis system, the jaundice analysis method comprising the steps of:

generating a first training data according to a first image data by a data processing module of the jaundice analysis system and correlating the first training data with a first category data by the data processing module;

training a target convolutional neural network module with the first training data correlating with the first category data by a deep learning module of the jaundice analysis system to obtain a trained convolutional neural network module; and generating a testing data according to an input image data by the trained convolutional neural network module of the jaundice analysis system, wherein the input image data comprises a second sclera image of a target subject, wherein the first image data comprises a first sclera image, wherein the testing data indicates a bilirubin concentration range of the target subject;

wherein the generating the first training data according to the first image data further comprises:

performing mirroring processing on the first image data by the data processing module to generate a mirroring image data, wherein the data processing module generates the first training data according to the mirroring image data.

11. The jaundice analysis method of claim 10, wherein the deep learning module obtains the trained convolutional neural network module by transfer learning.

12. The jaundice analysis method of claim 10, wherein the generating the first training data according to the first image data further comprises:

performing first cutting processing on the first image data by the data processing module to generate a first cutting image data, wherein the data processing module generates the first training data according to the first cutting image data.

13. The jaundice analysis method of claim 10, wherein the generating the first training data according to the first image data further comprises:

performing second cutting processing on the mirroring image data by the data processing module to generate a second cutting image data, wherein the data processing module generates the first training data according to the second cutting image data, wherein the second cutting image data has a specific image shape.

14. The jaundice analysis method of claim 13, wherein the generating the first training data according to the first image data further comprises:

performing third cutting processing on the second cutting image data by the data processing module to generate a third cutting image data, wherein the data processing module generates the first training data according to the third cutting image data.

15. The jaundice analysis method of claim 10, wherein the generating the first training data according to the first image data further comprising performing de-reflection processing on the first image data by the data processing module to generate a de-reflection image data, wherein the data processing module generates the first training data according to the de-reflection image data.

16. The jaundice analysis method of claim 10, further comprising the steps of:

generating, by the data processing module, a second image data according to the first image data; and generating a second training data according to the second image data by the data processing module and correlating the second training data with a second category data by the data processing module, wherein the deep learning module trains the target convolutional neural network module with the first training data correlating with the first category data and the second training data correlating with the second category data to obtain the trained convolutional neural network module.

17. The jaundice analysis method of claim 16, wherein the data processing module performs one of image translating processing, image rotating processing and image flipping processing on the first image data to generate the second image data.

18. The jaundice analysis method of claim 10, further comprising the steps of:

receiving, by a communication module of the jaundice analysis system, the input image data from a mobile device; and sending, by the communication module, the testing data to the mobile device.

* * * * *